(12) United States Patent
Masuhara et al.

(10) Patent No.: US 6,951,463 B2
(45) Date of Patent: Oct. 4, 2005

(54) DENTAL AND ORALOGIC COMPOSITION

(75) Inventors: Eiichi Masuhara, Tokyo-to (JP); Yoshinori Kadoma, Tokyo-to (JP); Junichi Yamauchi, Osaka-fu (JP); Koichi Okada, Okayama-ken (JP); Satoshi Yamaguchi, Osaka-fu (JP)

(73) Assignee: Kuraray Co., Ltd., Okayama-ken (JP)

( * ) Notice: Subject to any disclaimer, the term of this patent is extended or adjusted under 35 U.S.C. 154(b) by 517 days.

(21) Appl. No.: 09/728,121

(22) Filed: Dec. 4, 2000

(65) Prior Publication Data

US 2001/0002994 A1 Jun. 7, 2001

(30) Foreign Application Priority Data

Dec. 3, 1999 (JP) ............................................ 11-344938

(51) Int. Cl.[7] .......................... A61C 15/00; A61C 5/00; A61K 7/18; A61K 7/20
(52) U.S. Cl. .................. 433/216; 433/217.1; 433/228.1; 424/49; 424/53; 427/2.29; 427/2.3; 427/2.31; 427/255.18
(58) Field of Search .......................... 106/436; 502/227; 424/49; 433/216, 27.1, 228.1; 427/229, 2.3, 2.31

(56) References Cited

U.S. PATENT DOCUMENTS

| 5,738,840 A | * | 4/1998 | Richter ......................... 424/53 |
| 6,103,363 A | * | 8/2000 | Boire et al. .................. 428/325 |
| 6,165,256 A | * | 12/2000 | Hayakawa et al. ............ 106/13 |

FOREIGN PATENT DOCUMENTS

| GB | 2 257 439 A | * | 1/1993 |
| JP | 9-175923 | | 7/1997 |
| JP | 10 195382 | | 7/1998 |
| JP | 10-273412 | | 10/1998 |
| JP | 11 021127 | | 4/1999 |
| JP | 11 137573 | | 5/1999 |
| WO | WO 93/24103 | | 12/1993 |

OTHER PUBLICATIONS

Remington's Pharmaceutical Sciences, 1975, Mack Publishing Co. 15th Edition, pp. 384–385.*

* cited by examiner

*Primary Examiner*—Christopher S F Low
*Assistant Examiner*—Donna Jagoe
(74) *Attorney, Agent, or Firm*—Oblon, Spivak, McClelland, Maier & Neustadt, P.C.

(57) ABSTRACT

The first embodiment of present invention provides a composition, which includes:

(a) a photocatalytic titanium oxide or a photocatalytic titanium oxide precursor;

(b) at least one selected from the group including:
  a silicon compound having the following formula (I):

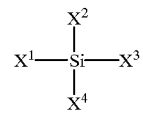

(I)

wherein $X^1$, $X^2$, $X^3$ and $X^4$ each independently represent an alkoxy group or a halogen atom,
  a hydrolyzate of the silicon compound (I), a silicone resin, silicone resin precursor and silica; and (c) a liquid medium. Another embodiment of the present invention provides a dental and oralogic composition, that includes a photocatalytic titanium oxide or a photocatalytic titanium oxide precursor. Another embodiment of the present invention provides a dental and oralogic composition, that includes a photocatalytic titanium oxide or a photocatalytic titanium oxide precursor, and a liquid medium. The composition of the present invention is particularly suitable in dental and oral care, and other embodiments of the present invention provide methods of making and using the above-described compositions.

7 Claims, No Drawings

DENTAL AND ORALOGIC COMPOSITION

BACKGROUND OF THE INVENTION

1. Field of the Invention

The present invention relates to a dental and oralogic composition containing a photocatalytic titanium oxide, and to a method of forming a photocatalytic titanium oxide-containing film on the surface of a dental material in or not in the mouth. More preferably, the invention relates to a dental and oralogic composition containing a photocatalytic titanium oxide, which is to be applied to dental materials including tooth crown restorative materials, dentures, denture bases, denture rebases, orthodontic bases, wires, bridges, mouth pieces, etc., to teeth, gums or oral mucous membranes, or to teeth having been restored with composite resin or coated with dental manicure, to thereby form a film of the composition on their surfaces. The film thus formed prevents the formation of biofilm, that is, dental plaque containing a large number of bacteria in the mouth, and prevents dental caries and periodontitis or prevents the promotion of such dental diseases. In addition, it prevents or retards the discoloration of teeth and dental materials to be caused by adhesion of cigarette tar or food deposits thereto, bleaches discolored teeth, and even prevents halitosis. The invention also relates to a method of forming such a photocatalytic titanium oxide-containing film on the surface of a dental material in or not in the mouth.

2. Discussion of the Background

Oral diseases include dental caries, gingivitis, periodontitis and other periodontal diseases (pyorrhea alveolaris, etc.), stomatitis, etc. Of these, dental caries is one typical disease of teeth, and it is believed to be caused by intrabuccal microorganisms that produce acid, which dissolves the enamel of teeth. Above all, it is said that *Streptococcus mutans* is a typical pathogen that causes dental caries. It is also said that peridontitis, which is a disease of peridentium, is caused by intrabuccal bacteria. In order to prevent and cure such diseases, it is important to immediately remove the dental plaque of intrabuccal bacteria adhered to the surface of teeth.

Expectant treatment has heretofore been employed to prevent and cure for each of the above types of oral diseases. For example, to prevent dental caries, fluorine-containing compounds are applied to teeth, or antibacterial agents are incorporated into dental materials. At present, however, these are not always effective or satisfactory in dental treatment. To restore and treat decayed teeth, dental materials such as dental metal (metal inlay), dental resin (cement for dental use), dental porcelain (porcelain inlay), composite resin (composite plastics for dental use) and others are used with which decayed teeth are restored or prosthetically treated. However, it is said that dental plaque of bacteria is readily formed on the surf aces of these dental materials. On the other hand, tooth brushing, mechanical dental scaling, and local application of chemicals to teeth and therearound have heretofore been recommended for preventing and curing periodontitis and other periodontal diseases. However, these are troublesome and time-consuming, and it is difficult to say that their effect is satisfactory for preventing and curing the dental diseases.

The surfaces of teeth and dental materials are often discolored due to the adhesion of cigarette tar or food deposits thereto, but no one knows an effective means for preventing the discoloration and for removing the adhered cigarette tar or food deposits, and a solution to these problems is desirable. Oral diseases such as dental caries, gingivitis, periodontitis and other periodontal diseases (pyorrhea alveolaris, etc.) cause halitosis, and it is likewise desirable to establish an effective means for preventing and removing halitosis.

Recently, a coating material that contains a photocatalytic titanium oxide has been proposed. This coating material is applied to the surfaces of appliances, tiles glass articles and others to form thereon an antibacterial, antifogging, antisoiling or deodorizing film owing to the photocatalytic activity of the titanium oxide in the material.

A liquid coating composition for teeth is known for applying such a photocatalytic titanium oxide to dental materials, which composition is prepared by mixing a photocatalytic titanium oxide with methyl α-cyanoacrylate and a resin component such as polymethyl methacrylate or the like (JP-A-175923/1997.) The published specification discloses that dental caries can be prevented by coating teeth with the coating composition. However, methyl α-cyanoacrylate used in the coating composition is extremely rapidly polymerized and cured by the moisture in air or by water in the mouth. The coating composition must therefore be applied to teeth within an extremely short period of time, and the coating composition is handled only with difficulty. In addition, the coating composition may not be completely safe for dental use in the mouth, since the composition contains methyl α-cyanoacrylate. Another problem with the coating composition is that its adhesion durability to teeth is poor, and the film that results from the coating composition is often peeled from teeth.

SUMMARY OF THE INVENTION

Accordingly, one object of the present invention is to provide a dental and oralogic composition, which is effective for preventing the adhesion of dental plaque onto the surfaces of teeth.

Another object of the present invention is to provide a dental and oralogic composition, which is effective for preventing the adhesion of dental plaque onto the surfaces of dental materials in the mouth and gums.

Another object of the present invention is to provide a dental and oralogic composition, which promotes the destruction and removal of dental plaque that has adhered to the surfaces of teeth and/or of dental materials in the mouth and gums.

Another object of the present invention is to provide a dental and oralogic composition, which effectively prevents and/or cures oral diseases and dental diseases such as dental caries, gingivitis, periodontitis and other peridental diseases (pyorrhea alveolaris, etc.), stomatitis, etc.

Another object of the present invention is to provide a dental and oralogic composition, which is easily handled and is highly safe.

Another object of the invention is to provide a dental and oralogic composition, which is effective for preventing and/or retarding the discoloration of teeth and dental materials caused by the adhesion of cigarette tar and/or food deposits thereto.

Another object of the invention is to provide a dental and oralogic composition, which is effective for bleaching discolored teeth.

Another object of the invention is to provide a dental and oralogic composition, which is effective for preventing and/or treating or removing halitosis.

Another object of the invention is to provide a method for forming a film that is effective for preventing and/or treating or removing halitosis.

Another object of the invention is to provide a method for forming a film that is effective for preventing and/or curing the dental diseases such as those mentioned above.

Another object of the invention is to provide a method for forming a film that is effective for preventing and/or retarding the discoloration of dental materials.

Another object of the invention is to provide a method for forming a film that is effective for bleaching discolored teeth.

Another object of the invention is to provide a method for forming a film on dental materials not in the mouth that is effective for preventing and/or curing the dental diseases such as those mentioned above.

Another object of the invention is to provide a method for forming a film on dental materials not in the mouth that is effective for preventing and/or retarding the discoloration of dental materials.

Another object of the invention is to provide a method for forming a film on dental materials not in the mouth that is effective for bleaching discolored teeth.

Another object of the invention is to provide a method for forming a film on dental materials not in the mouth that is effective for preventing and/or treating or removing halitosis.

These and other objects have been achieved by the present invention, the first embodiment of which provides a composition, which includes:

(a) a photocatalytic titanium oxide or a photocatalytic titanium oxide precursor;

(b) at least one selected from the group including:

a silicon compound having the following formula (I):

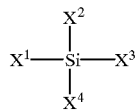

(I)

wherein $X^1$, $X^2$, $X^3$ and $X^4$ each independently represent an alkoxy group or a halogen atom, a hydrolyzate of the silicon compound (I), a silicone resin, silicone resin precursor and silica; and (c) a liquid medium.

Another embodiment of the present invention provides a dental and oralogic composition, that includes a photocatalytic titanium oxide or a photocatalytic titanium oxide precursor.

Another embodiment of the present invention provides a dental and oralogic composition, that includes a photocatalytic titanium oxide or a photocatalytic titanium oxide precursor, and a liquid medium.

Another embodiment of the present invention provides a film, which includes any of the above-described compositions.

Another embodiment of the present invention provides a method for making a film, that includes applying any of the above-described compositions to a surface of at least one selected from the group including teeth, gums, dental materials fitted in the mouth, oral mucous membranes, dental materials not in the mouth, and combinations thereof.

Another embodiment of the present invention provides a method for preventing or curing oral diseases or dental diseases, which includes:

applying any of the above-described compositions to a surface of at least one selected from the group including teeth, gums, dental materials fitted in the mouth, oral mucous membranes, dental materials not in the mouth, and combinations thereof, to form an applied composition;

drying the applied composition to form a photocatalytic titanium oxide-containing film on the surface; and exposing the film to light.

Another embodiment of the present invention provides a method for preventing or removing halitosis, which includes:

applying any of the above-described compositions to a surface of at least one selected from the group including teeth, gums, dental materials fitted in the mouth, oral mucous membranes, dental materials not in the mouth, and combinations thereof, to form an applied composition;

drying the applied composition to form a photocatalytic titanium oxide-containing film on the surface; and exposing the film to light.

Another embodiment of the present invention provides a method for preventing or retarding the discoloration of teeth or dental materials, which includes:

applying any of the above-described compositions to a surface of at least one selected from the group including teeth, gums, dental materials fitted in the mouth, oral mucous membranes, dental materials not in the mouth, and combinations thereof, to form an applied composition;

drying the applied composition to form a photocatalytic titanium oxide-containing film on the surface; and exposing the film to light.

Another embodiment of the present invention provides a method for bleaching discolored teeth, which includes:

applying any of the above-described compositions to a surface of at least one selected from the group including teeth, gums, dental materials fitted in the mouth, oral mucous membranes, dental materials not in the mouth, and combinations thereof, to form an applied composition;

drying the applied composition to form a photocatalytic titanium oxide-containing film on the surface; and exposing the film to light.

Another embodiment of the present invention provides a method for treating dental materials, which includes:

applying any of the above-described compositions to a surface of a dental material, to form an applied composition;

drying or baking or drying and baking the applied composition to form a photocatalytic titanium oxide-containing film on the surface; and exposing the film to light.

Another embodiment of the present invention provides a method for producing a dental and oralogic composition, which includes admixing a photocatalytic titanium oxide or a photocatalytic titanium oxide precursor with the dental and oralogic composition.

Another embodiment of the present invention provides a film, produced by a process that includes:

applying any of the above-described compositions to a surface, to form an applied composition; and drying or baking or drying and baking the applied composition to form a photocatalytic titanium oxide-containing film on the surface.

Another embodiment of the present invention provides an article, which includes a surface and the above-described film in contact with the surface.

Another embodiment of the present invention provides a method for preparing a dental and oralogic composition, which includes admixing:

(a) a photocatalytic titanium oxide or a photocatalytic titanium oxide precursor;

(b) at least one selected from the group including:
a silicon compound having the following formula (I):

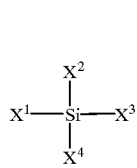

(I)

wherein $X^1$, $X^2$, $X^3$ and $X^4$ each independently represent an alkoxy group or a halogen atom,
a hydrolyzate of the silicon compound (I), a silicone resin, silicone resin precursor and silica; and
(c) a liquid medium.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The present inventors have continued to study the applicability of photocatalytic titanium oxide to dental use. The present inventors have found that a resin composition containing a photocatalytic anatase-type titanium dioxide, a (meth)acrylate monomer and a polymerization initiator is favorable to dental materials, and that, when the resin composite on is used in producing dental materials for dentures, denture rebases, orthodontic bases, denture restorative materials, mouth pieces, etc., or when it is applied to the surfaces of such dental materials and then exposed to light, then the smelly component having adsorbed or adhered to the dental materials in the mouth is decomposed to be odorless, and have already filed a patent application for the invention based on the findings (JP-A-273412/1998, the entire contents of which are hereby incorporated by reference).

The inventors have further studied, and, as a result, have found that a composition containing a photocatalytic titanium oxide or its precursor, at least one selected from a silicon compound such as an alkyl silicate or its hydrolyzed condensate, a silicone resin, a silicone resin precursor and silica, and a liquid medium is easily handleable and highly safe and has good film-forming ability on the surfaces of teeth and dental materials, like the dental resin composition disclosed in the above-mentioned JP-A-273412/1998, and that, when the composition is applied to the surfaces of teeth, dental materials or gums to form a film thereon and thereafter the thus-formed film is exposed to light, then the film acts to prevent the adhesion of dental plaque to the film-coated surfaces and to promote the destruction and removal of the dental plaque having adhered to the surfaces, thereby effectively preventing and curing oral diseases and dental diseases such as dental caries, gingivitis, periodontitis and other peridental diseases (pyorrhea alveolaris, etc.), stomatitis, etc.

In addition, the present inventors have found that a composition containing a photocatalytic titanium oxide and a liquid medium is also effective for preventing and curing such oral diseases and dental diseases, like the composition as above, and that, after the treatment with the composition for preventing and curing the diseases followed by exposure to light, the excessive composition can be readily removed from the treated site through washing with water. Moreover, we have found that a composition containing a photocatalytic titanium oxide precursor and a liquid medium is also effective like the compositions mentioned above.

The present inventors have also found that the above-mentioned compositions are effective for preventing and retarding the discoloration of teeth and dental materials to be caused by adhesion of cigarette tar and food deposits thereto, for bleaching discolored teeth, and for preventing and removing halitosis.

When any of the above-mentioned compositions is applied to the surfaces of dental materials not in the mouth, or when a photocatalytic titanium oxide sol or a photocatalytic titanium oxide precursor is applied thereto not in the mouth, and thereafter dried and/or baked, then a film containing photocatalytic titanium oxide and having the above-mentioned effects can be smoothly formed on the surfaces.

Preferred embodiments of the invention include the following (1)–(18):

(1) A dental and oralogic composition containing;
(a) a photocatalytic titanium oxide or a photocatalytic titanium oxide precursor,
(b) at least one selected from a silicon compound of the following general formula (I):

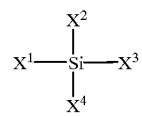

(I)

wherein $X^1$, $X^2$, $X^3$ and $X^4$ each independently represent an alkoxy group or a halogen atom, hydrolyzate of the silicon compound (I), a silicone resin, silicone resin precursor and silica, and
(c) a liquid medium.

(2) The dental and oralogic composition of above (1), wherein the ratio of the photocatalytic titanium oxide or photocatalytic titanium oxide precursor to at least one selected from the silicon compound (I), a hydrolyzate of the silicon compound (I), a silicone resin, a silicone resin precursor and silica falls between 20/1 and 1/100 in terms of the molar ratio of titanium atom/silicon atom.

(3) The dental and oralogic composition of above (1) or (2), wherein the photocatalytic titanium oxide precursor is a titanium alkoxide, and the silicone resin precursor is a silane compound and/or a silazane.

(4) A dental and oralogic composition containing a photocatalytic titanium oxide or a photocatalytic titanium oxide precursor.

(5) A dental and oralogic composition containing a photocatalytic titanium oxide or a photocatalytic titanium oxide precursor, and a liquid medium.

(6) The dental and oralogic composition of any of above (1) to (5), wherein the liquid medium is water, or a mixture of water and alcohol.

(7) The dental and oralogic composition of any of above (1) to (6), which contains a thickener.

(8) The dental and oralogic composition of any of above (1) to (7), which contains at least one of fine particles of a metal selected from silver, copper and zinc, and the metal salts.

(9) The dental and oralogic composition of any of above (1) to (8), which is to form a film on the surfaces of teeth, gums, dental materials fitted in the mouth, and/or oral mucous membranes, or to form a film on the surf aces of dental materials not in the mouth.

(10) A method for preventing and curing oral diseases and dental diseases, which comprises applying the dental and oralogic composition of any one of above (1) to (8) to the surfaces of teeth, gums, dental materials fitted in the mouth, and/or oral mucous membranes, then drying it to form a photocatalytic titanium oxide-containing film on the surf aces, and thereafter exposing the film to light.

(11) A method for preventing and removing halitosis, which comprises applying the dental and oralogic composition of any one of above (1) to (8) to the surf aces of teeth, gums, dental materials fitted in the mouth, and/or oral mucous membranes, then drying it to form a photocatalytic titanium oxide-containing film on the surf aces, and thereafter exposing the film to light.

(12) A method for preventing and retarding the discoloration of teeth and dental materials, which comprises applying the dental and oralogic composition of any one of above (1) to (8) to the surfaces of teeth, gums and/or dental materials fitted in the mouth, then drying it to form a photocatalytic titanium oxide-containing film on the surf aces, and thereafter exposing the film to light.

(13) A method for bleaching discolored teeth, which comprises applying the dental and oralogic composition of any one of above (1) to (8) to the surfaces of teeth, gums and/or dental materials fitted in the mouth, then drying it to form a photocatalytic titanium oxide-containing film on the surfaces, and thereafter exposing the film to light.

(14) A method for treating dental materials, which comprises applying the dental and oralogic composition of any one of above (1) to (8) to the surfaces of dental materials not in the mouth, then drying and/or baking it to form a photocatalytic titanium oxide-containing film on the surf aces of the dental materials, and thereafter exposing the film to light.

(15) Use of the dental and oralogic composition of any one of above (1) to (8) for forming a film.

(16) Use of a photocatalytic titanium oxide or a photocatalytic titanium oxide precursor for producing a dental and oralogic composition.

(17) Use of a photocatalytic titanium oxide or a photocatalytic titanium oxide precursor, and a liquid medium for producing a dental and oralogic composition.

(18) Use of the following (a) to (a) for producing a dental and oralogic composition:

(a) a photocatalytic titanium oxide or a photocatalytic titanium oxide precursor, (b) at least one selected from a silicon compound of the following general formula (I):

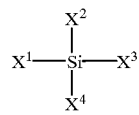
(I)

wherein $X^1$, $X^2$, $X^3$ and $X^4$ each independently represent an alkoxy group or a halogen atom, hydrolyzate of the silicon compound (I), a silicone resin, silicone resin precursor and silica, and (c) a liquid medium.

The "dental and oralogic composition" of the invention is meant to include compositions to be applied to teeth; dental materials including tooth crown restorative materials, dentures, denture bases, denture rebases, orthodontic bases, wires, bridges, mouth pieces, etc.; gums; oral mucous membranes; teeth having been restored with composite resin or coated with dental manicure. The dental and oralogic composition of the invention is applied to any of those objects to coat them.

The photocatalytic titanium oxide in the dental and oralogic composition of the invention is preferably titanium oxide which, when exposed to light, exhibits photocatalytic activity to promote the decomposition of organic matters, nitrogen oxides, etc. More preferably the photocatalytic titanium oxide is anatase-type titanium dioxide.

Depending on the morphology of the photocatalytic titanium oxide therein, the dental and oralogic composition of the invention is preferably grouped into the following compositions (A) and (B):

Composition (A)

The dental and oralogic composition of this type contains, as the component (a), a solid photocatalytic titanium oxide that exhibits photocatalytic activity by itself.

Preferably, the dental and oralogic composition (A) contains (a) a photocatalytic titanium oxide, (b) at least one selected from a silicon compound of above formula (I), a hydrolyzate of the silicon compound (I), a silicone resin, a silicone resin precursor and silica, and (c) a liquid medium; or contains (a) a photocatalytic titanium oxide and (c) a liquid medium.

Composition (B)

The dental and oralogic composition of this type contains, as the component (a), a photocatalytic titanium oxide precursor.

Preferably, the dental and oralogic composition (B) contains (a) a photocatalytic titanium oxide precursor, (b) at least one selected from a silicon compound of formula (I), a hydrolyzate of the silicon compound (I), a silicone resin, a silicone resin precursor and silica, and (c) a liquid medium or contains (a) a photocatalytic titanium oxide precursor and (c) a liquid medium.

The composition (A) and the composition (B) will be hereinafter generically referred to as "the composition of the invention" or simply as "the composition".

The photocatalytic titanium oxide in the composition (A) is preferably in the form of particles (fine powder) having a mean particle size of from 0.001 to 0.5 μm, more preferably from 0.005 to 0.1 μm, as it is highly dispersible not forming a sediment while stored or transported, and has high photocatalytic activity. These ranges include all values and subranges therebetween, including 0.0015, 0.002, 0.01, 0.05, 0.075, 0.25, 0.35 and 0.45 μm. Photocatalytic titanium oxide particles having a smaller particle size ensure higher photocatalytic activity. Therefore, in case where the composition (A) containing fine photocatalytic titanium oxide particles is directly applied to a predetermined site in the mouth and then exposed to light therein, it does not require any strong UV rays. Any weak UV rays that are safe to human bodies will be enough for ensuring the photocatalytic activity of the titanium oxide in the composition (A). Titanium oxide having been prepared in a low-temperature plasma process and therefore having especially high photocatalytic activity exhibits its photocatalytic activity even when exposed to visible rays of 400 nm or longer. For these reasons, the composition (A) of the type is preferable for use in the mouth.

The photocatalytic titanium oxide content of the composition (A) preferably falls between 0.05 and 40% by weight, more preferably between 0.1 and 20% by weight, in view of the dispersion stability of the ingredient, photocatalytic titanium oxide in the composition, the photocatalytic activity thereof, the easiness in applying the composition to substrates, and the strength of the coated film of the composition. These ranges include all values and subranges therebetween, including 0.07, 0.9, 1.1, 2, 5, 10, 15, 25, 30 and 35%.

Preferably, the photocatalytic titanium oxide precursor in the composition (B) includes titanium alkoxides, chelates, acetates, halides, and their hydrolyzates, and one or more of these may be present in the composition (B). Of these, especially preferred are titanium alkoxides and/or their hydrolyzates. Specific examples of titanium alkoxides are titanium tetraethoxide, titanium tetrabutoxide, titanium tetra-n-propoxide, titanium tetramethoxide, etc. One or more of these may be used. Some titanium oxide precursors such as titanium tetraethoxide and others are commercially available, for example, as titanium oxide sol, and such commercial products are also preferably used.

In the silicon compound of formula (I) that serves as the component (b) in the dental and oralogic composition of the invention, it is desirable that $X^1$, $X^2$, $X^3$ and $X^4$ each are independently an alkoxy group having from 1 to 4 carbon atoms, or a halogen atom such as chlorine, bromine or iodine atom. Preferable examples of the silicon compound (I) include tetraalkoxysilanes such as tetramethoxysilane, tetraethoxysilane, tetra-n-propoxysilane, tetraisopropoxysilane, tetrabutoxysilane, etc. Hydrolyzates of the silicon compound (I) include, for example, silanols derived from the above-mentioned tetraalkoxysilanes and their condensates (alkyl silicates), etc. Combinations of silicon compounds (I) may also be used.

Preferably, the silicone resin for the component (b) may be any of those composed of diorganosiloxane units only, those composed of monoorganosiloxane units only, those composed of diorganosiloxane units and monoorganosiloxane units, those composed of diorganosiloxane units, monoorganosiloxane units and triorganosiloxane units, those composed of diorganosiloxane units and triorganosiloxane units, those composed of monoorganosiloxane units and triorganosiloxane units, etc. The organic group bonding to the silicon atom in the siloxane units includes, for example, alkyl groups such as methyl group, ethyl group, propyl group, butyl group, etc.; alkenyl groups such as vinyl group, allyl group, etc.; aryl groups such as phenyl group, naphthyl group, etc.; and also the groups having a substituent, such as aralkyl groups, etc. Combinations may also be used.

Preferably, the silicone resin precursor for the component (b) includes, for example, organosilane compounds, organosilazane compounds and their low-molecular, hydrolyzed condensates, etc. The organosilane compounds include, for example, trifunctional monoorganosilanes such as methyltrimethoxysilane, ethyltriethoxysilane, propyltrichlorosilane, phenyltriethoxysilane, 3-methacryloxypropyltrimethoxysilane, etc.; difunctional diorganosilanes such as dimethyldiethoxysilane, phenylmethyldichlorosilane, diphenyldiethoxysilane, etc.; monofunctional triorganosilanes such as trimethylethoxysilane, trimethylchlorosilane, trioctadeoylchlorosilane, vinyldimethylethoxysilane, 3-methacryloxypropyldimethylmethoxysilane, 3-aminopropyldimethylethoxysilane, etc. Examples of the organosilazane compounds are hexamethyldisilazane, etc. Combinations are also possible.

The type of silica for the component (b) is not specifically defined, and any and every silica is usable for it.

The dental and oralogic composition of the invention may contain, for the component (b), one or more of the above-mentioned silicon compounds (I), their hydrolyzates, silicone resins, their precursors, and silica. Though not limited thereto, some preferable examples of the formulation of the dental and oralogic composition of the invention are mentioned below.

Preferable Examples of Formulation of Composition (A):

(A-1) Composition containing photocatalytic titanium oxide particles, and a tetraalkoxysilane or its hydrolyzate in a liquid medium.

(A-2) Composition containing photocatalytic titanium oxide particles, and a silicone resin in a liquid medium.

(A-3) Composition containing photocatalytic titanium oxide particles, and a silicone resin precursor such as an organosilane or its hydrolyzate, organosilazane or the like, in a liquid medium.

(A-4) Composition (suspension) containing photocatalytic titanium oxide particles and silica in a liquid medium.

(A-5) Composition containing a photocatalytic titanium oxide in a liquid medium.

Preferable Examples of Formulation of Composition (B):

(B-1): Composition containing a photocatalytic titanium oxide precursor such as a titanium tetraalkoxide or the like, and a tetraalkoxysilane or its hydrolyzate in a liquid medium.

(B-2) Composition containing a photocatalytic titanium oxide precursor such as a titanium tetraalkoxide or the like, and a silicone resin in a liquid medium.

(B-3): Composition containing a photocatalytic titanium oxide precursor such as a titanium tetraalkoxide or the like, and a silicone resin precursor such as an organosilane or its hydrolyzate, an organosilazane or the like, in a liquid medium.

(B-4): Composition containing a photocatalytic titanium oxide precursor such as a titanium tetraalkoxide or the like, and silica in a liquid medium.

(B-5): Composition containing a photocatalytic titanium oxide precursor such as a titanium tetraalkoxide or the like, in a liquid medium.

Preferably, the component (b) in the dental and oralogic composition of the invention contains at least 20 mol %, more preferably at least 50 mol % of a crosslinking silane or its hydrolyzate (a trifunctional or higher functional silane or its hydrolyzate), as it ensures the mechanical strength of the film of the composition. These ranges include all values and subranges therebetween, including 25, 30, 35, 40, 45, 55, 60, 65, 70, 75, 85, and 90 mol %. Preferably, the mol % of the crosslinking silane is based on the total moles of the component (b). Preferably, by use of the crosslinking silane, the composition can form a highly durable and practicable film in or not in the mouth, and, in addition, the adhesiveness of the composition to the substrate to which the composition is applied is enhanced.

Accordingly, it is preferable that the component (b) in the dental and oralogic composition of the invention contains a tetraalkoxysilane and/or its hydrolyzate (for example, as in the composition (A-1) and the composition (B-1) mentioned above), since the composition of the type has good film-forming capability and is easy to handle, and since the film of the composition formed on teeth, gums, dental materials and oral mucous membranes has high photocatalytic activity, high mechanical strength and high adhesiveness to substrates.

In addition, since the film of the composition in which the component (b) contains a tetraalkoxysilane and/or its hydrolyzate (especially the composition (A-1) mentioned above)

can exhibit high photocatalytic activity not only when exposed to UV rays but also even when exposed to visible rays that are highly safe to human bodies, the composition of the type is favorable to direct application to predetermined sites in the mouth.

Of such a tetraalkoxysilane and/or its hydrolyzate, especially preferred are tetraethoxysilane and/or its hydrolyzate. This is because the side product to be formed in hydrolysis and polycondensation of tetraethoxysilane is non-toxic ethyl alcohol. Therefore, the composition containing such tetraethoxysilane and/or its hydrolyzate has, in addition to the above-mentioned advantages, an additional advantage of high safety to human bodies.

In the dental and oralogic composition of the invention, the ratio of the photocatalytic titanium oxide or photocatalytic titanium oxide precursor to at least one selected from a silicon compound (I), a hydrolyzate of the silicon compound (I), a silicone resin, a silicone resin precursor and silica preferably falls between 20/1 and 1/100 in terms of the molar ratio of titanium atom/silicon atom, as the effect of the composition to decompose dental plaque and to retard the formation of dental plaque is high. More preferably, the ratio falls between 10/1 and 1/20. These ranges include all values and subranges therebetween, including 18/1, 15/1, 9/1, 5/1, 2/1, 1/1, 1/10, 1/25, 1/30, 1/40, 1/50, 1/70, 1/85 and 1/90.

The liquid medium for the dental and oralogic composition of the invention may be any and every one safe to human bodies. In general, however, preferred is water, or a mixture of water and alcohol, especially ethyl alcohol. More preferred for the liquid medium is a mixture of water and alcohol in a ratio by volume falling between 1/0.1 and 1/100, since the coatability of the composition containing it is good. These ranges include all values and subranges therebetween, including 1/0.2, 1/0.5, 1/0.9, 1/1, 1/1.5, 1/2, 1/10, 1/25, 1/30, 1/40, 1/50, 1/70, 1/85 and 1/90. In addition, after the composition containing such a water/alcohol mixture as the liquid medium has been applied to teeth, gums, oral mucous membranes and dental materials to form a film thereon, it is easy to remove the liquid medium from the coated composition. However, in case where the composition is not applied directly to the sites in the mouth but is applied to a dental material not in the mouth, then the liquid medium is preferably completely removed from the composition to form a film on the dental material, and thereafter the thus-coated dental material is fitted into the intended site in the mouth, any other organic solvent, and preferably not water or alcohol, may be used for the liquid medium for the composition. The organic solvent for the liquid medium preferably includes, for example, acetone, methyl ethyl ketone, ethyl acetate, chloroform, toluene hexane, etc.

The dental and oralogic composition of the invention may be in any form of dilute solutions, dilute dispersions, highly viscous solutions, highly viscous dispersions, pastes, shape-forming gels, etc., for which the type and the content of the photocatalytic titanium oxide or its precursor and at least one selected from silicon compounds (I), their hydrolyzates, silicone resins, silicone resin precursors and silica that constitute the composition shall be appropriately selected and controlled.

The advantage of the composition in the form of a dilute solute on or suspension is that a small amount of the composition can be applied to a predetermined site to form a thin and uniform film thereon and that, after the film is exposed to light to decompose the dental plaque around it, washing the cured film with water is easy.

To prepare a highly viscous solution or dispersion of the dental and oralogic composition of the invention, or to prepare a paste or a gel of the composition, a thickener may be added to the composition. The thickener easily increases the viscosity of the preparations. One or more of polyvinyl alcohol, polyalkylene glycols, glycerin, colloidal silica (silica aerosol, etc.) and the like serving as a thickener can be preferably used. The highly viscous solution or dispersion as well as the paste or gel of the composition, and preferably the paste or gel has the advantage of good handleability. Preferably, when the composition in that form is applied to a predetermined site in the mouth, it can be directly exposed to light without being dried, since the coated composition does not melt to flow away, and surely remains in the intended site to which it has been applied.

Optionally, the dental and oralogic composition of the invention may further contain at least one bactericidal metal component selected from silver, copper and zinc. The metal component may be any of the above-mentioned fine metal particles or metal salts. When the composition contains such a metal component, the composition inhibits the growth of bacteria around the surface of the substrate to which it has been applied. Accordingly, the composition inhibits more effectively the deposition or adhesion of dental plaque onto the site to which it has been applied. In addition, it will be easy to remove dental plaque decomposates from the composition applied site through washing with water. The amount of the metal component, if any, in the composition preferably falls between about 0.1 and 10% by weight of the total weight of the composition, as enhancing the handleability and the antibacterial and bactericidal effect of the composition and enhancing the durability of the film of the composition. This range includes all values and subranges therebetween, including 0.2, 0.5, 0.9, 1.0, 2, 3, 4, 5, 6, 7, and 9%. Mixtures of metal component are possible.

Also if desired, the dental and oralogic composition of the invention may contain a hydrolysis catalyst for the silicon compound (I) and the silicone resin precursor, a polycondensation catalyst, a pH controlling agent, a stabilizer, a colorant, a fluoride ion-releasing filler, an antibacterial agent, etc. Mixtures of these are possible.

The methods mentioned below are preferably employed for applying the dental and oralogic composition of the invention to teeth, gums, oral mucous membranes and dental materials.

For example, the composition (A) that contains photocatalytic titanium oxide particles may be applied to them according to the following methods:

(1) The composition (A) is applied to any of teeth, gums, oral mucous membranes, dental materials (tooth crown restorative materials, dentures, denture bases, denture rebases, orthodontic bases, wires, bridges, mouth places, etc.) fitted in the mouth, or teeth having been restored with composite resin or coated with dental manicure, and then optionally dried by exposing it to a gaseous blow (preferably a flowing gas stream) at a temperature not causing damage to the mouth to thereby form a photocatalytic titanium oxide-containing film on the substrate, and thereafter the film is exposed to light to express the photocatalytic activity of the photocatalytic titanium oxide therein.

(2) The composition (A) is applied to any of dental materials (tooth crown restorative materials, dentures, denture bases, denture rebases, orthodontic bases, wires, bridges, mouth pieces, etc.) not in the mouth, and then optionally dried and/or heated to thereby form a photocatalytic titanium oxide-containing film on the surface of the dental material, thereafter the film is exposed to light to express the photocatalytic activity of the photocatalytic titanium oxide therein, and the film-coated dental material is fitted into the mouth.

In the method (2), the steps of applying the composition (A) to the substrate, drying and heating it and then exposing it to light are all effected not in the mouth. In this, therefore, the composition (A) having been applied to the dental material may be dried and subjected to polycondensation at high temperatures, for example, at above 100° C. Such high-temperature treatment is preferable for ensuring the formation of a tight and abrasion-resistant film that contains the photocatalytic titanium oxide and silica, on the surface of the dental material.

In the methods (1) and (2), the film formed may be exposed to light by the use of a light emitter, but may be exposed to sun light or to light from a fluorescent lamp disposed in a room.

In order to convert a photocatalytic titanium oxide precursor such as a titanium alkoxide or the like into the corresponding photocatalytic titanium oxide (anatase-type titanium dioxide) having photocatalytic activity, it is necessary to bake the precursor at a temperature generally falling between 400 and 500° C. These ranges include all values and subranges therebetween, including 410, 420, 430, 440, 450, 460, 470, 480 and 490° C. Therefore, in case where the composition (B) is applied to dental materials to form thereon a film having photocatalytic activity, the dental materials must bear heating at the baking temperature. For such heat-resistant dental materials, for example, used are castable ceramics, dental porcelains and metals. A preferred method employable for the composition (B) includes applying the composition (B) to a heat-resistant dental material of, for example, castable ceramics, dental porcelains or metals (e. g., crowns, inlays, bridges, dentures, metal bases, wires, clasps, brackets, etc.), then optionally drying it, thereafter baking it at 400 to 500° C. to thereby convert the photocatalytic titanium oxide precursor to the corresponding photocatalytic titanium oxide and to form a film that contains the thus-converted photocatalytic titanium oxide, on the dental material, and then exposing the film to light to express the photocatalytic activity of the photocatalytic titanium oxide, and finally fitting the thus-coated dental material to a predetermined site in the mouth.

In place of using the composition (B) that contains a photocatalytic titanium oxide precursor along with the component (b) (selected from silicon compounds (I), their hydrolyzates, silicone resins, silicone resin precursors and/or silica), a solution or dispersion (including titanium oxide sol, etc.) that contains a photocatalytic titanium oxide precursor but does not contain the component (b) is also usable in the invention to attain the same result specifically, in case where such a solution or dispersion is applied to a heat-resistant dental material not in the mouth, then baked at 400 to 500° C. and thereafter exposed to light in the same manner as above, a film is formed on the dental material. Also in this case, the film formed on the dental material has photocatalytic activity, and the cured film thereon is effective for decomposing and removing dental plaque, for inhibiting dental plaque from adhering to the dental material, for preventing the dental material from being discolored and for preventing and removing halitosis. To that effect, the invention also encompasses the method of this case.

The photocatalytic activity of the photocatalytic titanium oxide-containing film that has been formed on the substrate of, for example, teeth, gums, oral mucous membranes, dental materials such as tooth crown restorative materials, dentures, denture bases, denture rebases, orthodontic bases, wires, bridges, mouth pieces, etc., and also teeth having been restored with composite resin or coated with dental manicure, is ensured to some degree even when the film is exposed to ordinary environmental light; however, in order to ensure higher photocatalytic activity of the film within a shorter period of time, it is preferable that the film is forcibly exposed to light by the use of a light emitter. In case where the photocatalytic activity of the film is lowered with the lapse of time, the film may be re-activated by exposing it to light. In particular, if the film is repeatedly exposed to light at regular intervals, it surely maintains its photocatalytic activity and is therefore extremely effective for inhibiting the deposition of dental plaque onto the surface of the film-coated substrate, for preventing the discoloration of the substrate, and for preventing halitosis. The method is especially preferable for detachable inlays, dentures, denture bases, cornus bridges, upper structures of implants, mouth pieces, etc,. These coated with the film are detached and taken out of the mouth, and may be exposed to light outside of in the mouth.

The source of light to which the photocatalytic titanium oxide-containing film is exposed preferably includes an ordinary visible light emitter for dental use, dental light, and other engineering light emitters, and also mercury lamps, xenon lamps, metal halide lamps, halogen lamps, fluorescent lamps, sun light, etc. Depending on the mode of light emission from it and the site to be irradiated with it, a suitable light source shall be selected and used.

Preferably, a film that contains a photocatalytic titanium oxide is formed on the substrate of, for example, teeth, gums, oral mucous membranes, dental materials such as tooth crown restorative materials, dentures, denture bases, denture rebases, orthodontic bases, wires, bridges, mouthpieces, etc., as well as teeth having been restored with composite resin or coated with dental manicure, and the film is then exposed to light to thereby express the photocatalytic activity of the titanium oxide therein, whereby the dental plaque formed on the substrate is decomposed, or deposition of dental plaque onto the substrate is retarded. To that effect, the photocatalytic titanium oxide-containing film formed on the substrate is effective for curing and preventing dental and oral diseases such as gingivitis, periodontitis and other peridental diseases (pyorrhea alveolaris, etc.), for preventing and retarding discoloration of teeth and dental materials, and for preventing and removing halitosis. In addition, the dental and oralogic composition of the invention may be applied to discolored teeth in the same manner as described herein, to thereby decompose the discoloring component and bleach the discolored teeth.

In case where the composition of the invention is again applied to the oral mucous membranes, teeth, gums, dental materials, and composite resin-restored or dental manicure-coated teeth that have been once cleaned with the composition to remove the dental plaque therefrom, thereby forming the photocatalytic titanium oxide-containing film of the composition on them, it is possible to prevent redeposition of dental plaque onto these substrates. The durability of the photocatalytic titanium oxide-containing film in the mouth varies, depending on the site coated with the film, but, in general, the film can maintain its photocatalytic activity at least for a few days to a few weeks or so. Even when the photocatalytic activity of the film is lowered with the lapse of time, the film can be reactivated by again exposing it to light in the manner described hereinabove.

EXAMPLES

Having generally described this invention, a further understanding can be obtained by reference to certain specific examples which are provided herein for purposes of illustration only and are not intended to be limiting unless otherwise specified.

Example 1

(1) Preparation of Dental and Oralogic Composition:

2 parts by weight of tetraethoxysilane, 55 parts by weight of water and 35 parts by weight of ethanol were mixed by stirring them. The pH of the resulting mixture was controlled to fall between 1.5 and 2, and the tetraethoxysilane therein was hydrolyzed to prepare a uniform solution 8 parts by weight of photocatalytic titanium oxide particles (Ishihara Sangyo's ST-01, having a mean particle size of 0.007 μm) were added thereto and uniformly dispersed to prepare a dental and oralogic composition. This was a dilute dispersion, in which the molar ratio of titanium atom/silicon atom was 10/1.

(2) Production of Denture Base Restored with Soft Rebase:

(i) 60 parts by weight of styrene-isoprene elastomer (Kuraray's HYBRAR-VSI), 38 parts by weight of lauryl methacrylate, 2 parts by weight of decanediol dimethacrylate, 0.2 parts by weight of camphorquinone, and 0.3 parts by weight of N,N-dimethylaminobutoxyethyl benzoate were mixed to prepare a soft rebase composition. This was a uniform, paste.

(ii) A polymethyl methacrylate denture base was polished on its surf ace that shall face an oral mucous membrane in its use. The polished depth corresponds to the thickness of the rebase to be applied to this. The polished surface of the denture base was coated high with the soft rebase composition that had been prepared in the previous step (i). The denture base thus coated high with the soft rebase composition was then fitted in the mouth of the patient, impressed therein, and then taken out of the mouth. The excessive soft rebase composition protruding out of the thus-processed denture base was removed. With that, the denture base was dipped in water at 25° C., and exposed to light from a dental light emitter (Morita's α-Light) for 10 minutes, while being shut out of air, to thereby polymerize and cure the soft rebase composition.

(3) Application of the Dental and Oralogic Composition to the Denture Base to form Film Thereon:

The denture base on which the rebase had been polymerized and cured in the above (2)(ii) was taken out of water, and then left at room temperature for 1 day. Next, the dental and oralogic composition that had been prepared in the above (1) was applied to the surface of the soft rebase of the denture base, and the liquid medium (water and ethanol) was evaporated away. Then, this was dried under heat at 90 to 100° C. for 1 hour, and a photocatalytic titanium oxide-containing film was thus formed thereon. Next, the film was exposed to light from a dental light emitter (Morita's α-Light) for 20 minutes to express the photocatalytic activity of the titanium oxide therein.

(4) Fitting of the Denture Base in the Mouth and Exposure Thereof to Light:

The denture base having been coated with the photocatalytic titanium oxide-containing film in the above (3) was fitted in the mouth of the patient, left as it was therein for 1 week and then taken out. The condition of the rebase of the denture bass was macroscopically checked for plaque deposition thereon and for discoloration of the rebase. It was found that only slight plaque deposited on the surface of the rebase and that the rebase was not discolored. The plaque deposited on the surface of the rebase was readily removed by washing with water.

Comparative Example 1

A denture base was coated with the same soft rebase as in the step (2) (ii) in Example 1. In this, however, the soft rebase was not coated with a photocatalytic titanium oxide-containing film. With that, the denture base was fitted in the mouth of the patient, left as it was therein for 1 week and then taken out. The condition of the rebase of the denture base was macroscopically checked for plaque deposition thereon and for discoloration of the rebase.

It was found that the amount of the plaque deposited on the surf ace of the rebase was much larger than that on the surface of the rebase in Example 1 and that the rebase was yellowed.

Example 2 and Comparative Example 2

(1) Preparation of Dental and Oralogic Composition:

2 parts by weight of tetraethoxysilane, 55 parts by weight of water and 35 parts by weight of ethanol were mixed by stirring them. The pH of the resulting mixture was controlled to fall between 1 and 2, and the tetraethoxysilane therein was hydrolyzed to prepare a uniform solution. 0.8 parts by weight of photocatalytic titanium oxide particles (Ishihara Sangyo's ST-01, having a mean particle size of 0.007 μm) were added thereto and uniformly dispersed to prepare a dental and oralogic composition. This was a dilute dispersion, which had a photocatalytic titanium oxide content of 0.9% by weight and a tetraethoxysilane hydrolyzate content of 2.1% by weight and in which the molar ratio of titanium atom/silicon atom was 1/1.

(2) Formation of Photocatalytic Titanium Oxide-containing Film:

(i) A photopolymerizable hard resin for tooth crowns (Kuraray's Estenia) was formed into a jacket crown for the right-side, admaxillary central incisor of the anterior teeth of a patient in accordance with the maker's instruction.

(ii) The dental and oralogic composition having been prepared in the previous stop (1) was applied thin to the surface of the jacket crown prepared in (i), by the use of a brush, and the solvent was evaporated away. Then, this was heated at 150° C. for 1 hour to thereby form a photocatalytic titanium oxide-containing film over the jacket crown (Example 2).

(iii) For comparison, another jacket crown for the left-side, admaxillary central incisor of the anterior tooth of the patient was prepared in the same manner as in the step (i), but this was not coated with the film, and was directly used as it was (Comparative Example 2).

(3) Fitting of the Jacket Crown in the Mouth and Check for Plaque Deposition Thereon:

(i) The jacket crown (this was prepared in the previous step (2) (ii) and was coated with the photocatalytic titanium oxide-containing film) was fitted to the right-side, admaxillary central incisor of the anterior teeth of the patient, by the use of a dental resin cement (Kuraray's Panavia) In addition, the jacket crown (this was prepared in the previous step (2) (iii) and was not coated the photocatalytic titanium oxide-containing film) was fitted to the left-side, admaxillary central incisor of the anterior teeth of the patient, also by the use of the same dental resin cement as above.

(ii) After three months, the patient was recalled, and a plaque-staining liquid (Lion's Plaque Tester) was applied to its anterior teeth. With that, the surfaces of the jacket crowns were macroscopically checked for plaque deposition thereon. Little plaque deposition was seen on the jacket crown (this had the photocatalytic titanium oxide-containing film formed thereon) fitted to the right-side, admaxillary central incisor of the anterior teeth of the patient; but much plaque deposition was seen on and around the jacket crown (this did not have the photocatalytic titanium oxide-containing film) fitted to the right-side, admaxillary central incisor of the anterior teeth of the patient, from the cervical margin to the gingival margin and therearound.

Example 3

(1) One part by weight of tetraethoxysilane, 2 parts by weight of titania sol (Ishihara Sangyo's STS-01) this is an aqueous sol that contains 30% by weight of titanium oxide having a mean particle size of 0.007 $\mu$m), 70 parts by weight of ethanol and 2 parts by weight of water were mixed to prepare a dental and oralogic composition. This was a dilute liquid, which had a photocatalytic titanium oxide content of 0.8% by weight and a tetraethoxysilane content of 1.3% by weight and in which the molar ratio of titanium atom/silicon atom was 5/3.

(2) The dental and oralogic composition having been prepared in the previous step (1) was applied to the admaxillary central incisor of the anterior teeth and to the gingival margin and therearound of a patient, by the use of a brush, and a light air blow was applied thereto to remove the liquid medium (water and alcohol). Using a dental light emitter (Ushio Electric's Litel), the area coated with the dental and oralogic composition was uniformly exposed to light for 2 minutes, and then washed with water. The process of applying the dental and oralogic composition, drying it with an air blow, exposing it to light and washing it with water was repeated further two times.

(3) Three days after the treatment of the above (2), the treated part was stained with a plaque-staining liquid (Lion's Plaque Tester), and macroscopically checked for plaque deposition thereon. Plaque deposition on the site coated with the dental and oralogic composition was significantly smaller than that on the site not coated with it. The result confirms that the dental and oralogic composition prepared in the above (1) is effective for removing plaque and for inhibiting re-deposition of plaque.

Example 4

(1) To the dental and oralogic composition having been prepared in the same manner as in the step (1) in Example 3, added was 0.1% by weight, relative to the weight of the composition, of polyvinyl alcohol, and dissolved therein to prepare a paste of the composition.

(2) The dental and oralogic paste that had been prepared in the previous step (1) was applied to the cervical margin and the gingival margin around the admaxillary and mandibular central incisors of a patient, and exposed to light from a dental light emitter (Ushio Electric's Litel) for 3 minutes.

(3) Three days after the treatment of the above (2), the treated part was stained with a plaque-staining liquid (Lion's Plaque Tester), and macroscopically checked for plaque deposition thereon. Plaque deposition on the site coated with the dental and oralogic paste was significantly smaller than that on the site not coated with it. The result confirms that the dental and oralogic paste prepared in the above (1) is effective for removing plaque and for inhibiting re-deposition of plaque.

Example 5

(1) To the dental and oralogic paste having been prepared in the step (1) in Example 4, further added was 2% by weight, relative to the weight of the paste, of fine silver particles (having a mean particle size of 2 $\mu$m) to prepare a silver-containing dental and oralogic paste.

(2) The silver-containing dental and oralogic paste that had been prepared in the previous step (1) was applied to the cervical margin and the gingival margin around the admaxillary and mandibular central incisors of a patient and to the pockets below the gingival margin, and exposed to light from a dental light emitter (Ushio Electric's Litel) for 3 minutes.

(3) Three weeks after the treatment of the above (2), the treated part was stained with a plaque-staining liquid (Lion's Plaque Tester), and macroscopically checked for plaque deposition thereon. Plaque deposition on the site coated with the dental and oralogic paste was significantly smaller than that on the site not coated with it. In addition, a small amount of the tissue of the part coated with the dental and oralogic paste was collected and checked for deposition of bacteria of *Streptococcus mutans* and *Candida alubicans*. Little deposition of the bacteria on the site was seen. The results confirm that the dental and oralogic composition that contains a photocatalytic titanium oxide and a silicon compound (I) along with fine silver particles is more effective for preventing and retarding dental plaque deposition and for killing bacteria.

Example 6

(1) From a metal frame of gold-silver-palladium alloy (GC's Castwell MC) and a dental porcelain (Shoflisha's Unibond Vintage), prepared was a metal-bonded porcelain bridge for admaxillary teeth.

(2) The metal-bonded porcelain bridge that had been prepared in the previous step (1) was sprayed thin with titanium oxide sol (Ishihara Sangyo's STS-01, having a titanium oxide content of 30% by weight), then dried, and baked at 500° C. Thus, this was coated with photocatalytic titanium oxide (anatase-type titanium dioxide).

(3) The metal-bonded porcelain bridge formed in the above step (2) was fitted into the mouth of a patient. After a half year, this was macroscopic ally checked for plaque deposition thereon, but little plaque deposited on it.

Example 7

(1) 2 parts by weight of the same photo catalytic titanium oxide particles (Ishihara Sangyo's ST-01) as in Example 1, 30 parts by weight of ethanol and 40 parts by weight of glycerin were mixed to prepare a dispersion. To this were added 15 parts by weight of polyoxyethylene glycol having a mean molecular weight of about 400 and 15 parts by weight of polyoxyethylene glycol having a mean molecular weight of about 4000, both serving as a thickener, and uniformly dispersed therein to prepare an adhesive, dental and oralogic paste.

(2) The dental and oralogic paste having been prepared in the above stop (1) was applied to all the teeth of a patient, from the right-side admaxillary premolar to the central incisor and also the gingival margin and the gums therearound, and was exposed to light from a dental light emitter (Ushio Electric's Litel) for 10 minutes.

(3) The mouth was fully washed with water to remove the excess paste, and the teeth and the gums therearound were dried with an air blow applied thereto. The site coated with the paste and exposed to light and the site not coated with it (this corresponds to the area from the left-side admaxillary premolar to the central incisor) were macroscopically checked for plaque deposition thereon, by the use of a plaque-staining liquid (Lion's Plaque Tester). The plaque deposition on the site coated with the paste was significantly smaller than that on the site not coated with it.

The bacteria inspection test made on the plaque that had been collected from the site coated with the paste revealed that bacteria of P. gingivalis and St. mutans were killed in the plaque.

Example 8

(1) 20 parts by weight of water, 40 parts by weight of glycerin, 10 parts by weight of the same photocatalytic titanium oxide powder as in Example 1, and 10 parts by weight of a silica fine powder (Aerosil 130) were mixed and uniformly dispersed to obtain a viscous dental and oralogic composition.

(2) The dental and oralogic composition having been prepared in the previous step (1) was applied thin to a right-half of an extracted discolored tooth (the admaxillary central incisor, the whole tooth crown of which was colored pale brown), by use of a brush. The left-half was stood for comparison as it was, without applying the composition. Then, the tooth was exposed to light for 5 minutes using a dental light emitter (Uni XSII, manufactured by Kulzer) and washed with water to remove the applied composition.

(3) After repeating the same operation as in the previous step (2) three times, the site applied with the dental and oralogic composition of this invention was compared in color tone through visual observation with the side not applied with it. As a result, in the site applied with the dental and oralogic composition of this invention, the original pale brown color became a pale yellow to white color, while in the site not applied with it, the color tone was not changed, i.e., the original brown color retained. The result confirms that the dental and oralogic composition of this invention is also effective for the purpose of bleaching the discolored tooth.

Comparative Example 3

(1) A paste was prepared from 30 parts by weight of ethanol, 40 parts by weight of glycerin, 15 parts by weight of polyoxyethylene glycol having a mean molecular weight of about 400 and 15 parts by weight of polyoxyethylene glycol having a mean molecular weight of about 4000, in the same manner as in the step (1) in Example 7. In this, however, the paste prepared did not contain photocatalytic titanium oxide particles.

(2) Also in the same manner as in Example 7, the paste prepared in the above step (1) was applied to the mouth of a patient, exposed to light, washed with water, and macroscopically tested with Plaque Tester for plaque deposition in the mouth. There was found no significant difference in the plaque deposition between the paste-coated site and the site not coated with the paste.

As described in detail hereinabove with reference to its preferred embodiments, the dental and oralogic composition of the invention is applied to teeth, gums, dental materials in the mouth, and teeth restored with composite resin or coated with dental manicure to prevent dental plaque deposition on them and even to promote destruction and removal of the dental plaque deposited an them, thereby effectively preventing and curing oral diseases and dental diseases such as dental caries, gingivitis, periodontitis and other peridontal diseases (pyorrhea alveolaris, etc.), stomatitis, etc.

In addition, the dental and oralogic composition of the invention effectively prevents or retards the discoloration of teeth and dental materials to be caused by adhesion of cigarette tar or food deposits thereto.

Further, the dental and oralogic composition of the invention is effectively used for bleaching discolored teeth.

Further, the dental and oralogic composition of the inventions effective for preventing and removing halitosis.

Further, the dental and oralogic composition of the invention is easy to handle and is safe.

Further, according to the method of the invention, a film effective for preventing and curing the dental diseases mentioned above, for preventing and retarding the discoloration of dental materials, for bleaching discolored teeth and for preventing halitosis can be easily formed on dental materials in and not in the mouth.

The dental and oralogic composition is capable of inhibiting dental plaque deposition and decomposing dental plaque to thereby prevent and cure dental diseases and oral diseases such as dental caries, gingivitis, periodontitis and other peridental diseases (pyorrhea alveolaris, etc.), stomatitis, etc., and is effective for preventing discoloration of teeth and dental materials and for preventing and removing halitosis; and the composition is particularly suitable for dental and oral care. The dental and oralogic composition preferably contains a photocatalytic titanium oxide or its precursor; at least one selected from silicon compounds such as tetraalkoxysilanes, silicone resins and their precursors and silica, and a liquid medium; or it contains a photocatalytic titanium oxide or its precursor and a liquid medium. The method for oral and dental care includes applying the composition to teeth, gums, oral mucous membranes or dental materials in the mouth, or applying the composition to dental materials not in the mouth, to thereby fix photocatalytic titanium oxide on them or form a photocatalytic titanium oxide-containing film on them.

Having now fully described this invention, it will be apparent to one of ordinary skill in the art that many changes and modifications can be made thereto without departing from the spirit or scope of the invention as set forth herein.

This application is based on Japanese Patent Application No. 344938/1999, filed Dec. 3, 1999, the entire contents of which are hereby incorporated by reference, the same as if set forth at length.

What is claimed as new and desired to be secured by Letters Patent of the United States is:

1. A method comprising:
   applying to a surface selected from the group consisting of teeth, gums, a dental material fitted within the mouth, and an oral mucous membrane, a composition that comprises:
   (a) a photocatalytic titanium oxide or a photocatalytic titanium oxide precursor;
   (b) at least one compound selected from the group consisting of:
      a silicon compound having the following formula (I):

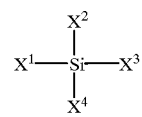

(I)

wherein $X^1$, $X^2$, $X^3$ and $X^4$ each independently represent an alkoxy group or a halogen atom,
   a hydrolyzate of said silicon compound (I),
   a silicone resin,
   silicone resin precursor,
   and silica; and
   (c) a liquid medium;

wherein a ratio of (a) to (b) ranges from 20/1 to 1/100 in terms of moles of titanium atoms in (a)/moles of silicon atoms in (b);

drying said applied composition to form a photocatalytic titanium oxide containing film on said surface; and exposing said film to light.

2. The method of claim 1, comprising applying said composition into the mouth of a subject having a dental or oral disease or onto a dental material fitted within the mouth of said subject.

3. The method of claim 1, comprising applying said composition into the mouth of a subject having halitosis or onto a dental material fitted within the mouth of said subject.

4. The method of claim 1, comprising applying said composition into the mouth of a subject having discolored teeth or onto a dental material fitted within the mouth of said subject.

5. The method of claim 1, comprising applying said composition into the mouth of a subject having a dental or oral disease or onto a dental material fitted within the mouth of said subject.

6. The method of claim 1, which is a method for bleaching discolored teeth.

7. The method of claim 1, wherein said composition is applied to a dental material, which is fitted within the mouth.

* * * * *